US010058344B2

(12) United States Patent
Raybin et al.

(10) Patent No.: US 10,058,344 B2
(45) Date of Patent: Aug. 28, 2018

(54) APPARATUS FOR TISSUE DISSECTION WITH SUCTION RING

(71) Applicant: Boston Scientific Scimed, Inc., Maple Grove, MN (US)

(72) Inventors: Samuel Raybin, Marlborough, MA (US); Paul Smith, Smithfield, RI (US); Naroun Suon, Lawrence, MA (US); Daniel Lang, North Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 256 days.

(21) Appl. No.: 14/204,808

(22) Filed: Mar. 11, 2014

(65) Prior Publication Data

US 2014/0276909 A1    Sep. 18, 2014

Related U.S. Application Data

(60) Provisional application No. 61/798,690, filed on Mar. 15, 2013, provisional application No. 61/777,988, filed on Mar. 12, 2013.

(51) Int. Cl.
*A61B 17/3205* (2006.01)
*A61B 17/32* (2006.01)
(Continued)

(52) U.S. Cl.
CPC .. *A61B 17/320016* (2013.01); *A61B 1/00094* (2013.01); *A61B 1/00101* (2013.01);
(Continued)

(58) Field of Classification Search
CPC ...... A61B 17/320016; A61B 17/32056; A61B 1/00137; A61B 17/30; A61B 2017/00269;
(Continued)

(56) References Cited

U.S. PATENT DOCUMENTS 2,115,298 A * 4/1938 Brown .................. A61B 17/26
                                                      15/339
3,896,810 A    7/1975 Akiyama
(Continued)

FOREIGN PATENT DOCUMENTS

DE    101 26 062 A1    5/2001
EP    2 057 973 A1    10/2007
(Continued)

OTHER PUBLICATIONS

International Search Report and Written Opinion for corresponding international Application No. PCT/US2014/023598 dated Jun. 26, 2014, (14 pages).

*Primary Examiner* — Jing Ou
(74) *Attorney, Agent, or Firm* — Bookoff McAndrews, PLLC

(57) ABSTRACT

A medical device may include a housing. The housing may include an outer wall, an inner wall spaced from the outer wall, and a cavity between the outer wall and the inner wall. The cavity may be in fluid communication with a lumen configured to adjust pressure within the cavity. The medical device may also include a cutting tool configured to move from extending around an outer surface of the housing to entering the cavity of the housing.

14 Claims, 10 Drawing Sheets

(51) Int. Cl.
*A61B 1/00* (2006.01)
*A61B 17/00* (2006.01)
*A61B 17/30* (2006.01)

(52) U.S. Cl.
CPC .... *A61B 1/00137* (2013.01); *A61B 17/00234* (2013.01); *A61B 17/30* (2013.01); *A61B 17/32056* (2013.01); *A61B 2017/00269* (2013.01); *A61B 2017/00296* (2013.01); *A61B 2017/306* (2013.01); *A61B 2017/308* (2013.01)

(58) Field of Classification Search
CPC .......... A61B 2017/306; A61B 1/00101; A61B 1/00094; A61B 17/00234; A61B 2017/00296; A61B 2017/308
See application file for complete search history.

(56) References Cited

U.S. PATENT DOCUMENTS

| | | | |
|---|---|---|---|
| 4,730,617 A | 3/1988 | King | |
| 5,171,233 A * | 12/1992 | Amplatz | A61B 17/221 604/540 |
| 5,643,281 A * | 7/1997 | Suhocki | A61B 17/32056 606/106 |
| 5,976,073 A * | 11/1999 | Ouchi | A61B 1/00089 600/129 |
| 6,015,415 A * | 1/2000 | Avellanet | A61B 18/14 606/110 |
| 6,059,719 A | 5/2000 | Yamamoto et al. | |
| 6,068,603 A * | 5/2000 | Suzuki | A61B 10/04 600/564 |
| 6,306,081 B1 | 10/2001 | Ishikawa et al. | |
| 7,507,200 B2 * | 3/2009 | Okada | A61B 1/012 600/104 |
| 7,736,302 B2 | 6/2010 | Matsuno | |
| 2001/0005775 A1 * | 6/2001 | Samson | A61B 5/04485 600/376 |
| 2001/0053909 A1 | 12/2001 | Nakada et al. | |
| 2002/0035311 A1 * | 3/2002 | Ouchi | A61B 1/00089 600/175 |
| 2003/0191413 A1 | 10/2003 | Damarati | |
| 2004/0210111 A1 * | 10/2004 | Okada | A61B 1/00087 600/127 |
| 2005/0261711 A1 | 11/2005 | Okada et al. | |
| 2006/0270906 A1 | 11/2006 | Matsuno | |
| 2007/0118166 A1 | 5/2007 | Nobis et al. | |
| 2007/0260112 A1 * | 11/2007 | Rahmani | A61B 17/12013 600/104 |
| 2008/0108871 A1 | 5/2008 | Mohr | |
| 2010/0056861 A1 * | 3/2010 | Spivey | A61B 1/00087 600/106 |
| 2011/0130744 A1 | 6/2011 | Kassab et al. | |
| 2013/0018367 A1 * | 1/2013 | Wu | A61B 18/0218 606/21 |
| 2013/0110109 A1 * | 5/2013 | Nguyen | A61B 17/32056 606/46 |
| 2013/0165959 A1 | 6/2013 | Smith et al. | |

FOREIGN PATENT DOCUMENTS

| | | |
|---|---|---|
| GB | 1405025 | 9/1975 |
| JP | 9-187415 | 7/1997 |
| JP | 2003-52713 A | 2/2003 |
| JP | 2010063721 A | 3/2010 |
| JP | 2010246849 A | 11/2010 |
| WO | WO 03/082121 A2 | 10/2003 |
| WO | WO 2012/040865 A1 | 4/2012 |

* cited by examiner

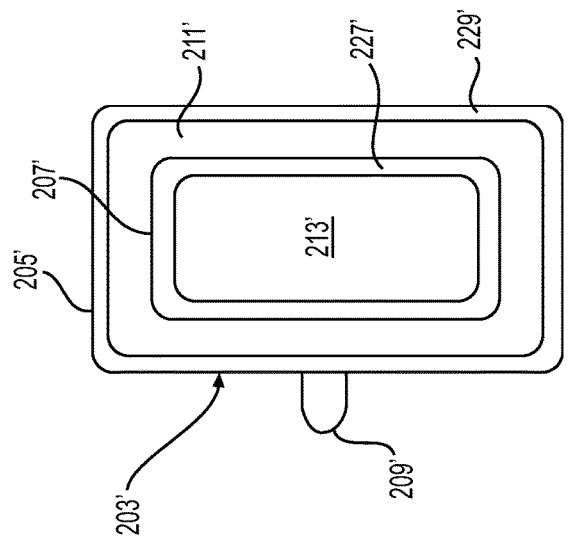
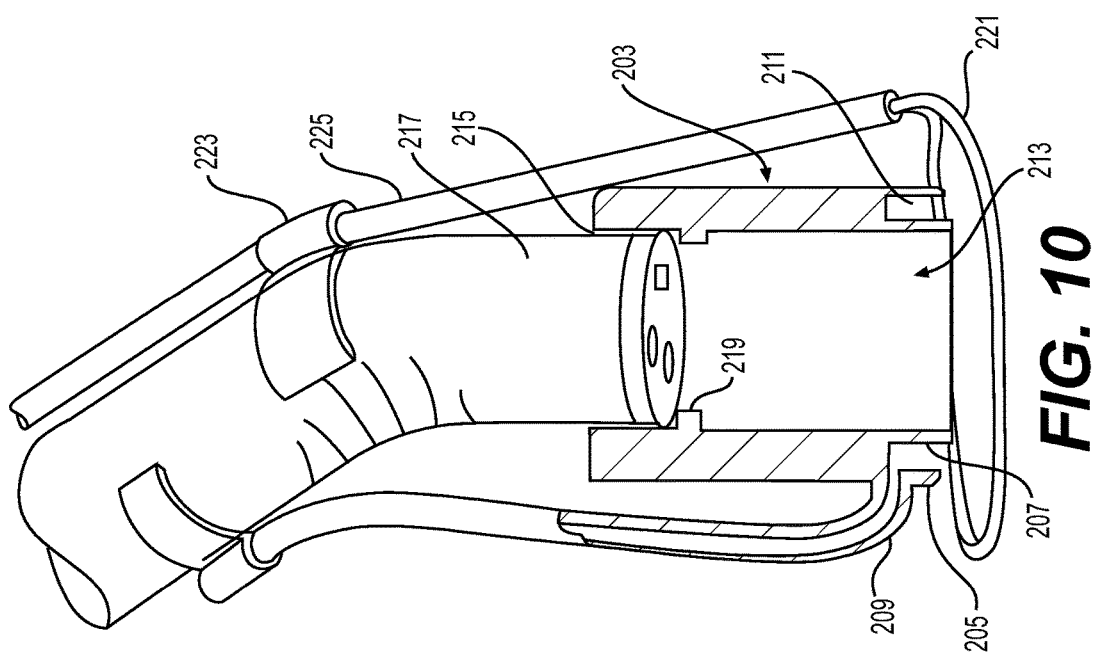

APPARATUS FOR TISSUE DISSECTION WITH SUCTION RING

CROSS-REFERENCE TO RELATED APPLICATIONS

This application claims the benefit of priority from U.S. Provisional Application No. 61/777,988, filed on Mar. 12, 2013, and U.S. Provisional Application No. 61/798,690, filed on Mar. 15, 2013, each of which is incorporated by reference herein in its entirety.

DESCRIPTION OF THE INVENTION

Field of the Disclosure

The present disclosure generally relates to a medical instrument, and more particularly to an apparatus for tissue resection.

Background

A wide variety of medical techniques and instruments have been developed for diagnosis and/or treatment within a patient's body, such as the gastrointestinal (GI) tract. For example, endoscopic mucosal resection (EMR) is a minimally invasive technique used for removing, e.g., malignant/non-malignant lesions and/or otherwise unwanted tissue. Endoscopic medical procedures, for example EMR, may excise sessile adenomas (i.e., tumors attached to a bodily surface) in an anatomical lumen. Such procedures often require the dissection of one tissue plane while leaving an underlying tissue plane intact. When performing these procedures, it is desirable to cleanly cut and retrieve a uniform tissue sample of sufficient size, particularly where a pathology study of the sample might be necessary. In addition, it is desirable for the resection to leave clean margins at the treatment site in order to minimize any further disruption of the surrounding anatomy.

If the adenoma is flat against a lumen wall, however, excising the adenoma can be difficult. In such cases, one of several techniques may be used to raise the flat adenoma so that it may be excised appropriately without harming underlying tissue layers. For instance, forceps can be used to raise the flat adenoma. Also, injections of a solution into, e.g., the submucosal or an underlying tissue layer can create a space or opening under the tissue, creating a buffer zone. The space lifts the flat adenoma above the underlying tissue to facilitate removal, and minimizes mechanical or electrocautery damage to the deeper tissue layers.

These conventional techniques and instruments, however, have many disadvantages and/or limitations. For example, perforation is a key concern as it poses a serious safety risk the patient. The present disclosure is described to overcome one or more of the above limitations and/or other shortcomings in the art.

SUMMARY OF THE DISCLOSURE

The present disclosure relates to a embodiments of apparatus and methods for tissue resection, which may reduce the risk of perforating underlying tissue layers by, e.g., lifting and separating the mucosa from the muscularis, around the perimeter of the lesion or other unwanted tissue.

According to aspects of the present disclosure, a medical device may include a housing including an outer wall, an inner wall spaced from the outer wall, and a cavity between the outer wall and the inner wall. The cavity may be in fluid communication with a lumen configured to adjust pressure within the cavity. The medical device may also include a cutting tool configured to move from extending around an outer surface of the housing to entering the cavity of the housing.

Additionally or alternatively, the cutting tool may include a snare; the snare may be configured to form a loop around the outer surface of the housing; the loop may be configured to enter the cavity of the housing as the loop closes; the outer wall of the housing may include a distal end, the inner wall of the housing may include a distal end, and the distal end of the outer wall may be proximal to the distal end of the inner wall; a distal end of the cavity may extend between the distal end of the outer wall and the distal end of the inner wall; at least one of the distal end of the inner wall and the distal end of the outer wall may include a straight edge; and/or at least one of the distal end of the inner wall and the distal end of the outer wall may be substantially rectangular.

According to aspects of the present disclosure, a medical device may include a housing including an outer wall having a distal end, and an inner wall spaced from the outer wall, the inner wall having a distal end. The distal end of the outer wall may be disposed proximally from the distal end of the inner wall. The housing may include a cavity between the outer wall and the inner wall. The cavity may be in fluid communication with a lumen configured to adjust pressure within the cavity. The medical device may also include a cutting tool configured to move from extending around an outer surface of the housing to exerting a radially inwardly directed force against the inner wall of the housing.

Additionally or alternatively, the cutting tool may include a snare; the snare may form a loop around the outer surface of the housing; the radially inwardly directed force may be a compressive force around the inner wall of the housing; the cutting tool may be configured to move into direct contact with the inner wall of the housing; at least one of the distal end of the inner wall and the distal end of the outer wall may include a straight edge; and/or at least one of the distal end of the inner wall and the distal end of the outer wall is substantially rectangular.

According to aspects of the present disclosure, a method of resecting tissue from within a patient may include advancing a medical device to a target location within the patient. The medical device may include a housing including an outer wall, an inner wall spaced from the outer wall, and a cavity between the outer wall and the inner wall. The cavity may be in fluid communication with a lumen configured to adjust pressure within the cavity. The medical device may also include a cutting tool extending around at least a portion of the housing and being spaced apart from the housing. The method may include disposing a distal end of the housing adjacent a tissue wall. The method may also include applying suction to the cavity to draw at least one layer of the tissue wall into the cavity. The method may also include resecting a portion of tissue drawn into the cavity with the cutting tool by moving the cutting tool into the cavity of the housing.

Additionally or alternatively, moving the cutting tool into the cavity of the housing may include closing a loop of the cutting tool to bring the loop into the cavity of the housing; the method may include bringing the cutting tool into engagement with the inner wall of the housing; drawing at least one layer of the tissue wall into the cavity may include drawing at least one substantially straight portion of the at least one layer of the tissue wall into the cavity; and/or drawing at least one layer of the tissue wall into the cavity may include drawing a substantially rectangular portion of the at least one layer of the tissue wall into the cavity.

Other aspects and features of the disclosure will be evident from reading the following detailed description of the preferred embodiments, which are intended to illustrate, not limit, the disclosure.

BRIEF DESCRIPTION OF THE DRAWINGS

The present disclosure is further described in the detailed description which follows, in reference to the drawings, by way of non-limiting examples of preferred embodiments of the present disclosure, in which like characters represent like elements throughout the several views of the drawings.

FIG. 10 shows a cross-sectional side view of an apparatus, in accordance with aspects of the present disclosure.

FIG. 11 shows an end view of a housing, in accordance with aspects of the present disclosure.

DETAILED DESCRIPTION OF THE EMBODIMENTS

Reference will now be made in detail to the exemplary embodiments of the disclosure illustrated in the accompanying drawings. Wherever possible, the same reference numbers will be used throughout the drawings to refer to the same or like parts.

Figure 1:
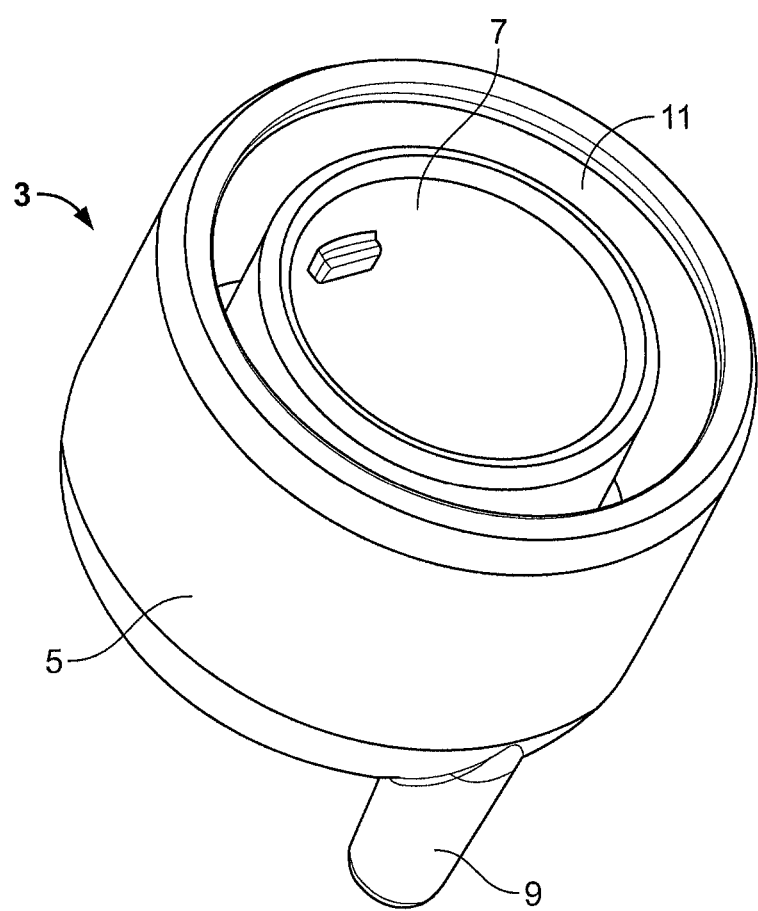
FIG. 1 illustrates a perspective view of an exemplary tissue resection apparatus according to an embodiment of the present disclosure.
Figure 2:
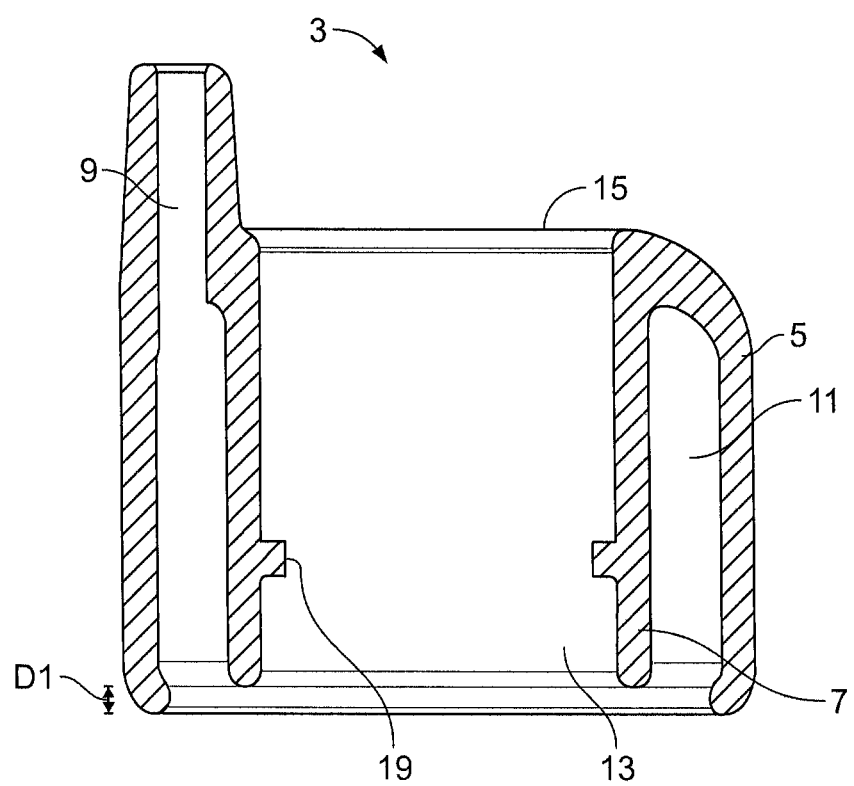
FIG. 2 is a cross-sectional view of the exemplary tissue resection apparatus of FIG. 1.

The present disclosure relates to an apparatus for endoscopic treatment, which may reduce the risk of perforating an underlying tissue layer, e.g., by lifting and separating the tissue layer intended for resection from the underlying layer, which is not intended for the resection. FIG. 1 and FIG. 2 illustrate an exemplary tissue resection apparatus 1, according to an embodiment of the present disclosure. As shown, the apparatus may include a housing 3 having an outer wall 5 and an inner wall 7 disposed within the housing 3. The inner wall 7 is surrounded by the outer wall 5 and separated by a specific distance so that there is a cavity 11 or a hollow gap (referred hereinafter as the "cavity") formed between the outer wall 5 and the inner wall 7. In one embodiment, the cavity 11 may be substantially annular or completely annular, extending completely about chamber 13. The distal end of the housing 3 is opened so that the housing 3 is adapted to be placed against a surface of tissue. The housing 3 further includes a connection to a suction source, for example the port 9, for applying suction in the cavity 11 to draw tissue into the cavity 11.

In some embodiments, the space surrounded by the inner wall 7 may be hollow, forming a hollow chamber 13, as depicted in FIG. 2. As will be described in further detail below, the housing 3 may include a proximal opening 15, providing access to the hollow chamber 13, so that an elongated tubular member (not shown in FIG. 2) can be inserted into the hollow chamber 13.

Figure 3:
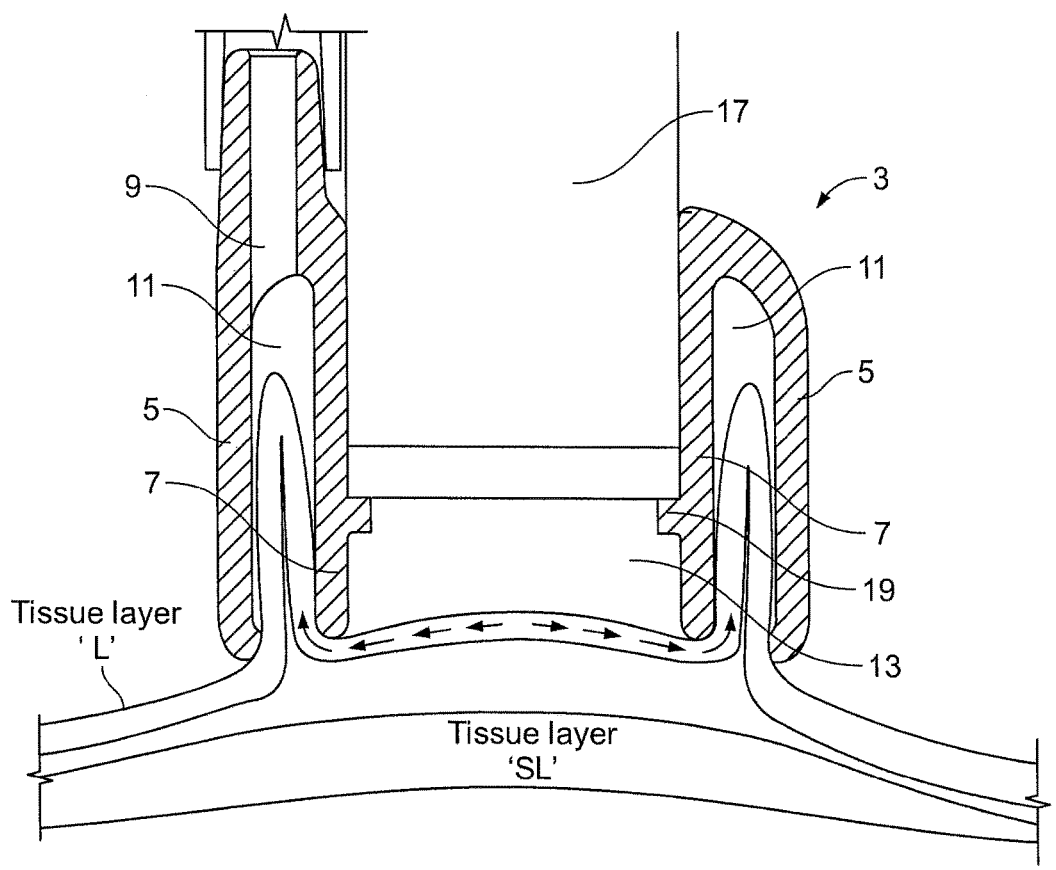
FIG. 3 is a cross-sectional view of the exemplary tissue resection apparatus including an endoscope therein and in cooperating with tissue, according to an embodiment of the present disclosure.

FIG. 3 illustrates a cross-sectional view of the apparatus 1 being placed against a tissue layer "L". When the apparatus is placed against the surface of targeted tissue layer "L", the suction applied from the suction source (not shown) via the port 9 draws in the targeted tissue "L" into the cavity 11, thereby forming a ridge of tissue, as illustrated in FIG. 3. In one embodiment, port 9 may be in fluid communication with cavity 11, so that a vacuum applied to port 9 may be realized throughout cavity 11. As shown in FIG. 1, e.g., port 9 may be offset relative to a longitudinal axis of housing 3 such that cavity 13 (discussed below) may receive tubular member 17 therein. A portion of port 9 may be configured to extend away from a proximal end of housing 3. The raised ridge of tissue drawn into the cavity 11 may facilitate snaring or other resection methods. The cavity 11 may be preferably narrow so that the non-targeted sub tissue layer (e.g., tissue layer "SL") is excluded from being drawn up into the cavity, thereby reducing the risk of perforating the SL tissue layer.

In some embodiments, the housing 3 may include a substantially cylindrical shape. In such a case, a continuous circular cavity will be formed between the outer wall 5 and the inner wall 7, and the tissue drawn into the cavity 11 will form a circumferential ridge of tissue surrounding a substantially flat tissue surface in the middle, as illustrated in FIG. 3. However, it should be noted that the housing 3 can be in any shape suitable for forming the cavity 11 for drawing tissue therein. For example, housing 3 may include a square or rectangular configuration shown in, e.g., FIGS. 7A, 7B, and 8. More particularly, housing 3 defines an opening having at least one straight edge to facilitate removal of tissue via a tessellation technique.

As briefly described above, the apparatus 1 may include a hollow chamber 13 for accommodating an elongated tubular member (e.g., tubular member 17). In an aspect, the apparatus 1 may be configured as an endoscopic cap, and the elongated tubular member 17 may be an endoscope with various endoscope functionalities, including visualization, illumination, flushing, irrigation, suction, and the like, and using a variety of tools through its working channels (not shown). Those of ordinary skill in the art will understand that tubular member 17 may include any suitable introduction sheath known in the art.

In some embodiments, one or more internal working channels may be included inside the tubular member 17 for receiving endoscopic instruments, such as an optical scope or as an aspiration path connected to the suction source. It should be noted that the internal working channels may have non-circular cross-sectional shapes, and may be in any shapes depending on the types of endoscopic instrument and/or application of the working channel(s). Further, the tubular member 17 may include a number of additional lumens for receiving control wires, which may extend from various control sources (e.g., actuation handle, knobs, steering controls, etc.) disposed at the proximal end of tubular member 17 through the tubular member 17.

An external shape and dimension of the tubular member 17 may be substantially the same as the hollow chamber 13. In some embodiments, the dimension (e.g., width) of the tubular member 17 may be slightly larger than the size of the hollow chamber 13 in order to facilitate a tight fitting of the tubular member 17 into the hollow chamber 13. In such cases, the surroundings of the proximal opening of the hollow chamber 13 and/or the inner wall 7 may be made of a flexible material that is elastically deformable to accommodate the larger tubular member 17 into the hollow chamber 13. In some embodiments, the tubular member 17 may be made of a flexible material that is elastically deformable, so that the tubular member 15 can be snuggly fitted into the hollow chamber 13. In addition, one or more ledges or ridges 19 may be formed on an interior wall of the hollow chamber 13 to prevent the tubular member 17 from passing through the entire hollow chamber 13. A position of ledges or ridges 19 along inner wall 7 may be varied as desired to alter a position of tubular member 17 relative to housing 3. Also, in some other embodiments, the apparatus 1 may be configured so that the elongated tubular member 17 can pass completely through the hollow chamber 13, which will allow for extension and retraction of the apparatus 1 relative to the tubular member 17 (e.g., endoscope). In such embodiments, therefore, ledges or ridges 19 may be excluded.

Figure 4:
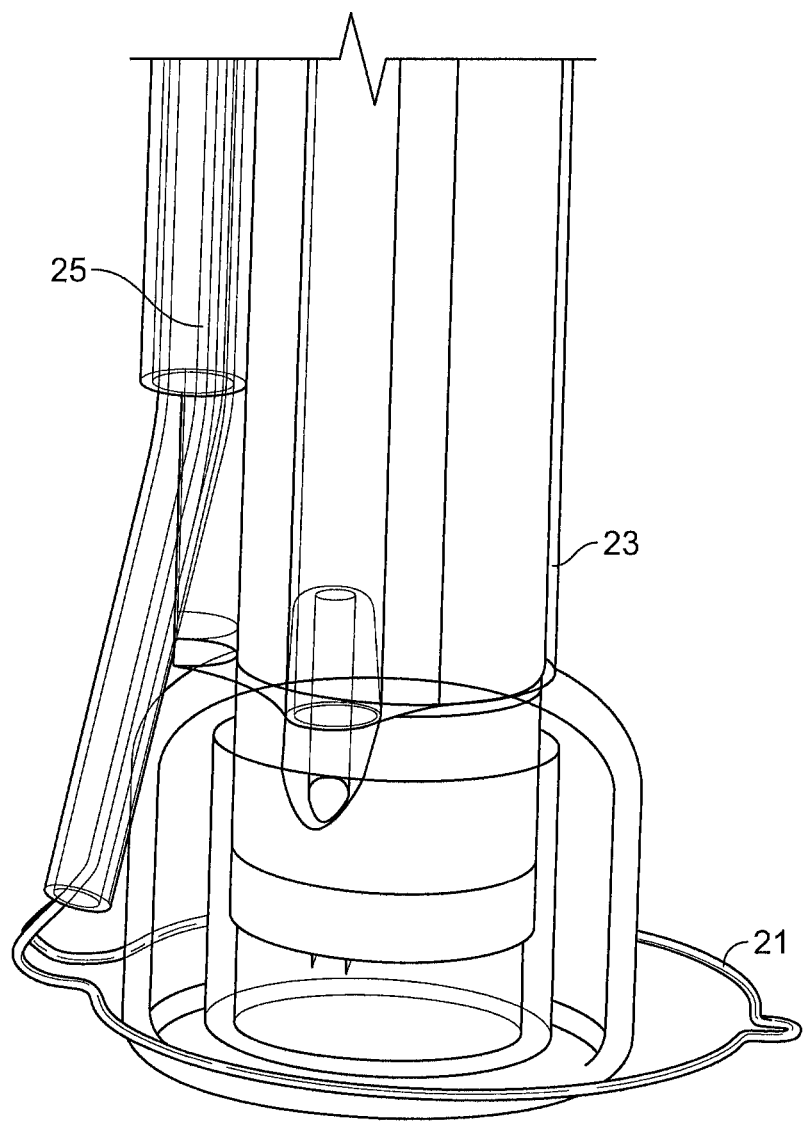
FIG. 4 is a schematic view of an exemplary tissue resection apparatus in combination with a suitable cutting device, in accordance with another embodiment of the present disclosure.

FIG. 4 illustrates an exemplary embodiment of the apparatus 1 equipped with a snare 21. Those of ordinary skill in the art will understand that any suitable cutting device may be used in conjunction with apparatus 1. As shown, snare 21 can be opened and preloaded around the exterior of the apparatus 1 prior to drawing in the tissue. When the tissue layer ("L") is drawn into the cavity 11 as shown in FIG. 2, the snare 21 can be closed around the base of the raised circumferential ridge of the drawn up tissue for resection. In this example, the tubular member 17 may be surrounded by a sheath 23, which may contain at least one auxiliary working channel 25. The sheath 23 may include a flexible tubular member extending proximally away from a proximal end of the housing 3. Auxiliary working channel 25 may include a lumen in the aforementioned sheath 23 or another tubular member operably coupled to the sheath 23. For instance, the auxiliary working channel 25 may accommodate the snare 21. It should be appreciated that the sheath 23 may include a plurality of auxiliary working channels 25 for various other functionalities. For example, one of the working channels may function as the aspiration path between the port 9 and the suction source (not shown). Additional auxiliary working channels may be included in the sheath 23 to accommodate various other instruments and functionalities. Although the apparatus 1 and the tubular member 17 have been described in the context of an endoscope cap with a snare, it is contemplated that the tubular member 17 also may be any other medical device, such as a catheter or guiding tube that includes any number of the features and characteristics disclosed herein. Further, various tissue dissection/resection tools may be also used in conjunction with the apparatus 1 for tissue resection or other endoscopic treatment.

Figure 5:
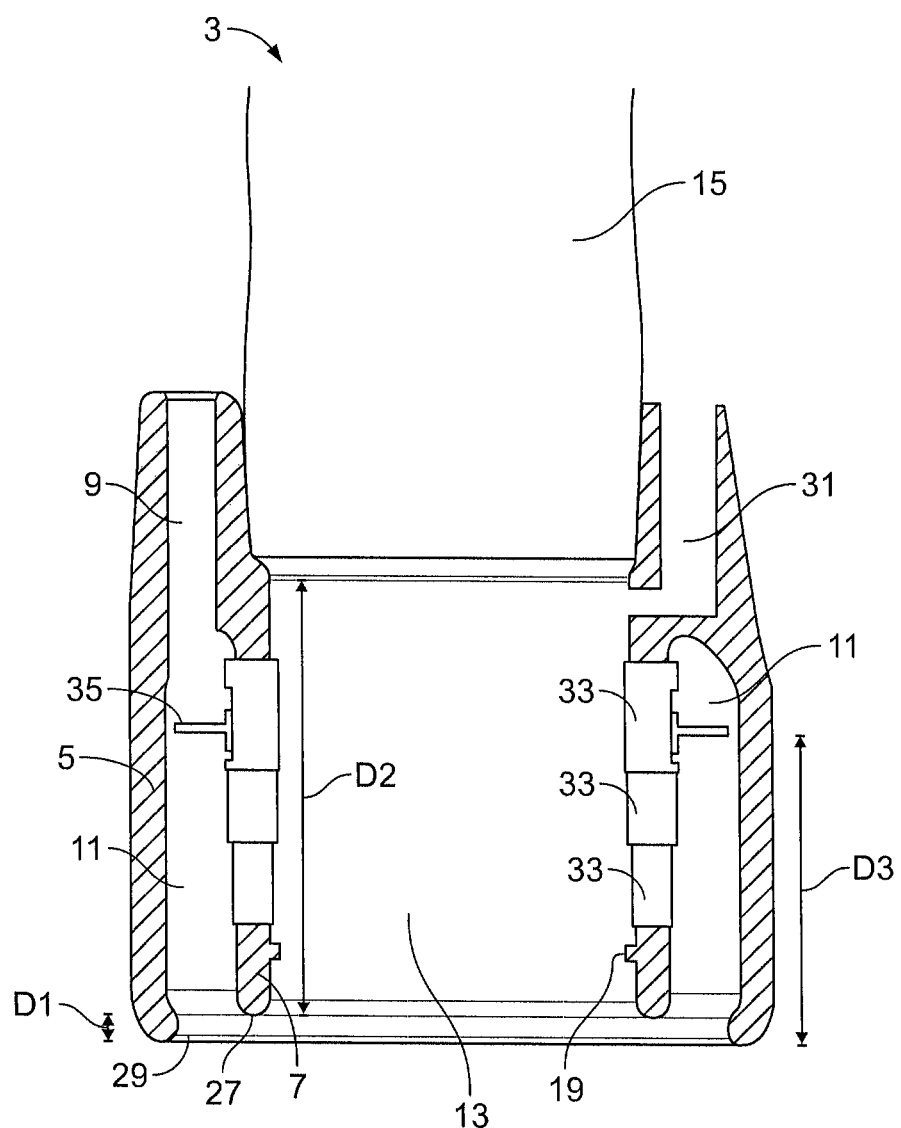
FIG. 5 is a cross-sectional view of an exemplary tissue resecting apparatus, according to a further aspect of the present disclosure.

FIG. 5 illustrates additional details of the apparatus 1. The distal end portion of the outer wall 5 may be rounded and bent towards the inner wall 7 at a predetermined angle. This angle may promote drawing in the tissue positioned underneath the hollow chamber 13 (i.e., the tissue layer "L" surrounded by the most distal end/tip 27 of the inner wall 7) so that tissue underneath the hollow chamber 13 becomes taut as illustrated by the arrows in FIG. 3.

In some embodiments, the distal most end/tip 27 of the inner wall 7 is substantially co-planar with the distal most end/tip 29 of the outer wall 5. In other embodiments, however, the tip 27 of the inner wall 7 may be recessed towards the proximal end of the housing 3 relative to the tip 29 of the outer wall 5 as shown in FIG. 5. In other words, the tip 29 of the outer wall 5 is extended closer to the surface of the tissue layer ("L") than the tip 27 of the inner wall 7. In this configuration, the hollow chamber 13 may not be completely isolated from the suction applied via the port 9 by the inner wall 7. Accordingly, when the suction is applied from the suction source, the tissue layer ("L") enclosed within the tip 29 of the outer wall 5 may be drawn up (i.e., lifted) to the level of the tip 27 of the inner wall 7 initially. When the tissue layer ("L") contacts the tip 27 of the recessed inner wall 7, a seal may be formed so that the cavity 11 is isolated from the hollow chamber 13. In other words, the recessed inner wall 7 elevates the tissue layer ("L") approximately equal to the vertical distance ("D1" shown in FIG. 5) between the tip 29 of the outer wall 5 and the tip 27 of the inner wall 7.

Once the tissue layer "L", which is enclosed within the housing 3, is elevated and the hollow chamber 13 is isolated from the suction applied via the port 9, the tissue layer "L" may be further drawn into the cavity 11 to form a ridge of tissue surrounding the substantially flat tissue underneath the hollow chamber 13. It is contemplated that the elevation of tissue within the housing 3 can prevent the snare 21 from snagging on the inner wall 7 during resection procedure, e.g.

Further, in some embodiments, a distal tip 27 of inner wall 7 may be longer than tip 29 of outer wall 5. For example, with reference to FIG. 8, apparatus 80 may include an outer wall 82 and an inner wall 84. Inner wall 84 may be configured to extend distally further than outer wall 82 to ensure proper suction on the targeted tissue is maintained. In other embodiments, however, the distal ends of both inner and outer walls 82 and 84 may be flush with one another.

In some embodiments, the hollow chamber 13 may be provided with its own aspiration port 31 to provide negative/positive pressure in the hollow chamber 13. For example, negative pressure may be applied to draw tissue into the disclosed apparatus. In the embodiments where positive pressure is applied, the positive pressure may be used to expel tissue lodged in the disclosed apparatus or otherwise in contact with the disclosed apparatus. In such embodiments, a tubular member 15 may include an internal or an auxiliary working channel (not shown) providing an aspiration path for the hollow chamber 13. In some embodiments, one or both of ports 9 and 31 may be used to introduce, e.g., irrigation or insufflation, to a location within a patient's body.

In some embodiments, the length of the inner wall 7 (e.g., the vertical length "D2") may be adjustable, such that the tip 27 of the inner wall 7 may be extended and/or retracted in distal and proximal directions relative to wall 5. It is contemplated that the adjustable inner wall 7 enables controlling the amount of elevation of the tissue required for creating the seal (e.g., isolating the hollow chamber 13 from the port 9), at which point the tissue will be drawn into the cavity 11 to form the ridge of tissue. Adjusting inner wall 7 may also allow sufficiently separating tissue layers so that an underlying tissue is not perforated during a resection procedure. When it is not necessary to elevate the tissue prior to forming the ridge of tissue, the inner wall 7 may be extended in the distal direction so that the tip 27 of the inner wall 7 is substantially co-planar with the tip 29 of the outer wall 5, thereby creating instant isolation of the hollow chamber 13 from the suction applied via the port 9. Those of ordinary skill in the art will readily recognize that outer wall 5 may be also configured to be adjustable in substantially the same manner as inner wall 7.

Various types of mechanisms and configurations may be employed in implementing the adjustable inner wall 7 or outer wall 5. For the purposes of efficiency, the adjustable mechanisms will be only described relative to inner wall 7, however those of ordinary skill will understand that the same principles may be applied to outer wall 5. In an exemplary embodiment, the inner wall 7 may include a plurality of telescoping segments 33 that are arranged to slide, e.g., in and out relative to one another, as depicted in FIG. 5. In this example, the elongated tubular member 15 may be used in exerting the force necessary for extending and/or retracting the telescoping segments 33. For instance, the elongated member 15 may include one or more grooves that may selectively couple with one or more of ridges 19 or may abut a fixed portion of the inner wall 7, such that the vertical length ("D2") of the inner wall 7 may be controlled by pushing in and/or pulling out the tubular member 15. In some other embodiments, some portion of the inner wall 7 may be formed as a screw thread, a helical ridge, a spiral groove and/or appropriate gearing mechanisms, such that the distance between the tip 27 of the inner wall 7 and the tip 29 of the outer wall 5 is adjusted by applying rotational force to move the inner wall 7 in the proximal or distal directions relative to outer wall 5. For example, a portion of an external wall of the elongated tubular member 15 may include a screw thread corresponding to a screw thread on the inner wall 7, so that rotational force applied to the tubular member 15 facilitates moving the inner wall 7 relative outer wall 5. In some other embodiments, other control means that are operable via the working channel and/or the lumen may be used in implementing the adjustable inner wall 7. Such other control means may include, e.g., an electric motor disposed in the housing 3 or the tubular member 15 controlled via the control lines extending through the lumen in the tubular member 15.

Figure 6A:
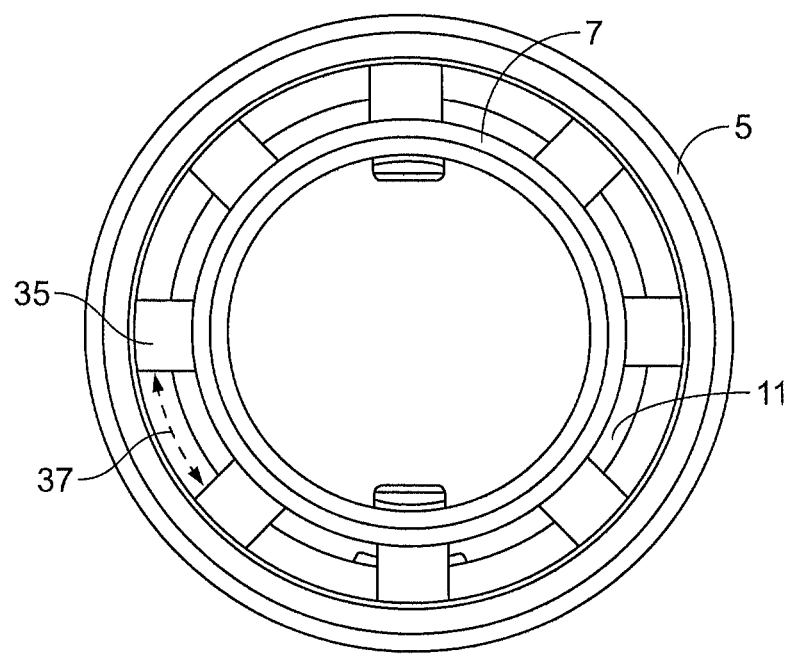
FIG. 6A is a top view of the apparatus of FIG. 5.
Figure 6B:
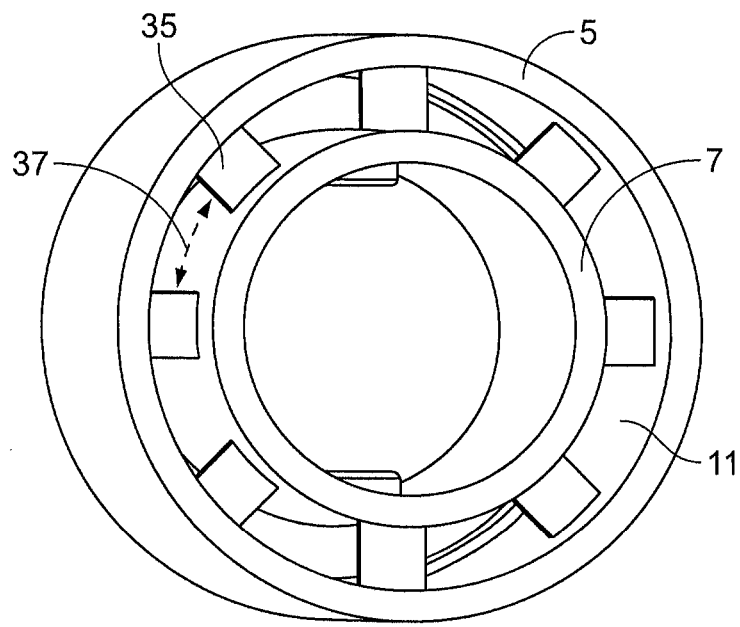
FIG. 6B is a bottom view of the apparatus of FIG. 5.

The size (e.g., a width or volume) of the resected tissue may be controlled by the amount of tissue drawn into the cavity 11. Accordingly, in some embodiments, the apparatus 1 may further include a number of depth limiters 35 disposed within the cavity 11 to adjust and/or control the amount of tissue drawn into the cavity 11, as shown in FIGS. 5, 6A and 6B. The depth limiters 35 may include a plurality of blocks, panels, or other suitable structures that extend between the outer wall 5 and the inner wall 7 at a specific depth (e.g., "D3" shown in FIG. 5) within and around the cavity 11. The plurality of depth limiters 35 may be arranged relative to each other in such a way that a plurality of gaps 37 is formed between every two adjacent depth limiters 35. The size of each gap 37 formed between the depth limiters 35 should be sufficient to maintain the air-flow necessary for drawing tissue into the cavity 11 while preventing the tissue from passing through the gap 37. The size of the gaps 37 formed between each of the depth limiters 35 may vary depending on the type of tissues and/or the type of resection procedures.

In some embodiments, the depth of the vertical distance ("D3") of the depth limiters relative to the tip 29 of the outer wall 5 may be adjustable. By way of an example, some portion of the inner wall 7 may include one or more slots for receiving the depth limiters 35, so that the depth limiter 35 can be moved distally or proximally within the cavity 11. Similarly, the depth limiters may extend from or be received in an inner surface of outer wall 5. One of the internal or the auxiliary working channels may be used for extending a control mechanism for moving depth limiters 35 within the cavity 11. The control mechanism may be a rotatable rod or a cable configured to push and pull the depth limiters 35 along the cavity 11. In some other embodiments, the depth limiters 35 may utilize a screw thread, a helical ridge, a spiral grove and/or other suitable mechanisms configured for adjusting the position of depth limiters 35. The control mechanism may also be an electrical motor disposed in the housing 3 or the tubular member 15, providing sufficient force to move the depth limiters 35 as desired.

Further, the plurality of depth limiters 35 may be formed as a single piece structure in order to simplify the control mechanism for adjusting the depth limiter 35. Alternatively, each depth limiter 35 may be separately adjustable by providing an independent control mechanism for each depth limiter 35. This configuration may allow for more precise control over the amount of tissue being drawn into the cavity 11 as each of the depth limiters 35 around the cavity 11 may be adjusted to be at differing depths. It should be appreciated that various other control mechanisms and configurations may be used in implementing the adjustable depth limiters 35.

Figure 7B:
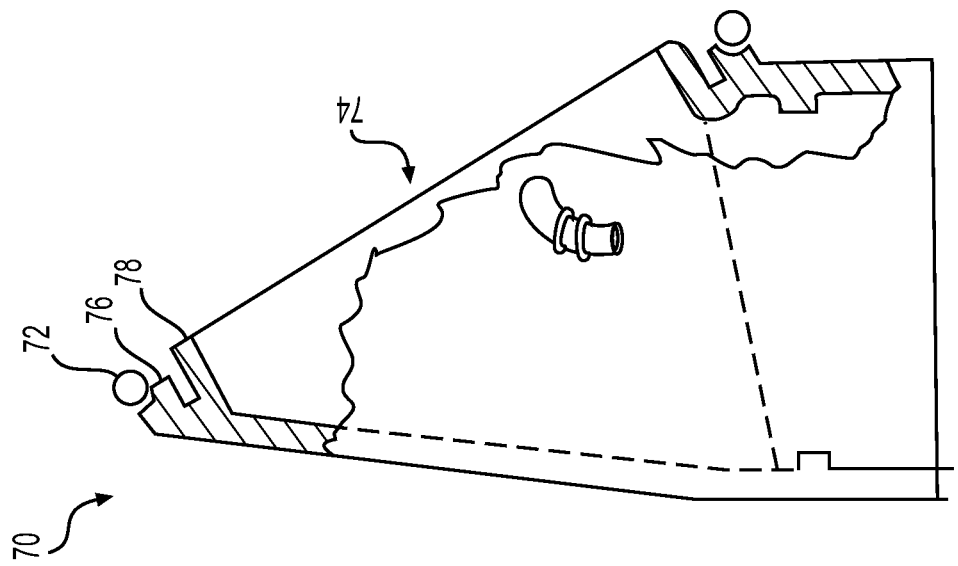
FIGS. 7A-7B depict an alternate embodiment of an apparatus in accordance with a further embodiment of the present disclosure.
Figure 7A:
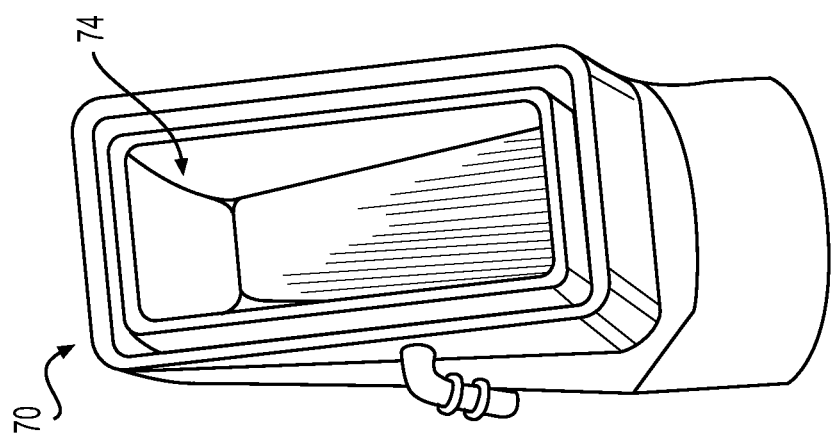
Figure 8:
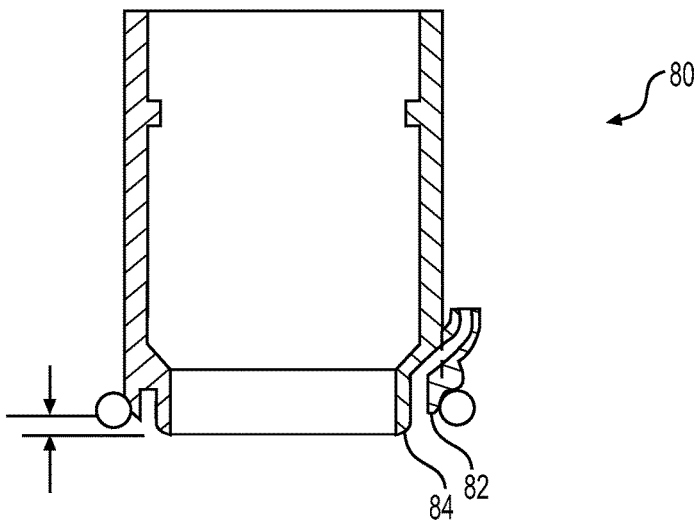
FIG. 8 depicts a further embodiment of an apparatus in accordance with the present disclosure.

In some embodiments, the disclosed apparatus may include suitable cutting and/or ligating instruments. For example, as shown in FIG. 7B, the device 70 may be provided with a cutting tool 72 disposed about a periphery of opening 74. Cutting tool 72 may include any suitable tool known in the art. For example, in one embodiment, cutting tool 72 may include a snare, which may or may not include electro-cautery capabilities. Further, cutting tool 72 may include a ligating band or shuttling wire in some embodiments. Further, although the depicted embodiment illustrates that cutting tool 72 is disposed adjacent outer wall 76, those of ordinary skill in the art will understand that cutting tool 72 may be disposed adjacent inner wall 78.

Figure 9A:
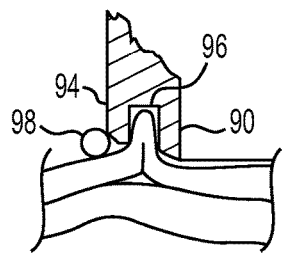
FIGS. 9A-9C depict exemplary structures to facilitate separating a first tissue layer from a second tissue layer, in accordance with the present disclosure.
Figure 9B:
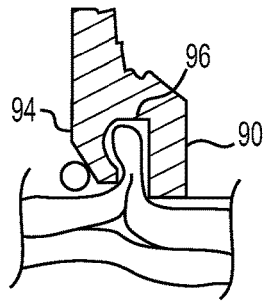
Figure 9C:
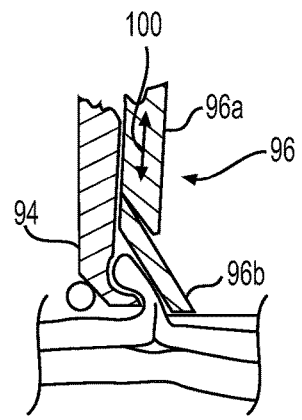

FIGS. 9A-9C depict embodiments of an alternative apparatus in accordance with the present disclosure. For example, as shown in FIG. 9A, inner wall 90 may be longer than outer wall 94. Together inner wall 90 and outer wall 94 may define a groove 96 therebetween for receiving tissue. A cutting tool 98 (as discussed above) may be disposed adjacent outer wall 94. A distal end of inner wall 90 may be angled away from outer wall 94. Further, an outer, distal edge of outer wall 94 may include a bevel or chamfer. Groove 96 may include a generally rectangular cross-sectional configuration.

With reference to FIG. 9B, e.g., a distal end of inner wall 90 may be substantially planar. However, outer wall 94 may include a configuration that angles outer wall 94 toward inner wall 90. Turning now to FIG. 9C, inner wall 96 may include a first portion 96*a* movably coupled to a second portion 96*b*. First portion 96*a* may be configured to move reciprocally in the directions of arrow 100. Second portion 96*b* may be configured to transition between a first configuration and a second configuration, wherein in the second configuration, the second portion 96*b* is configured to trap tissue between second portion 96*b* and an inner surface of outer wall 94.

Figure 13:
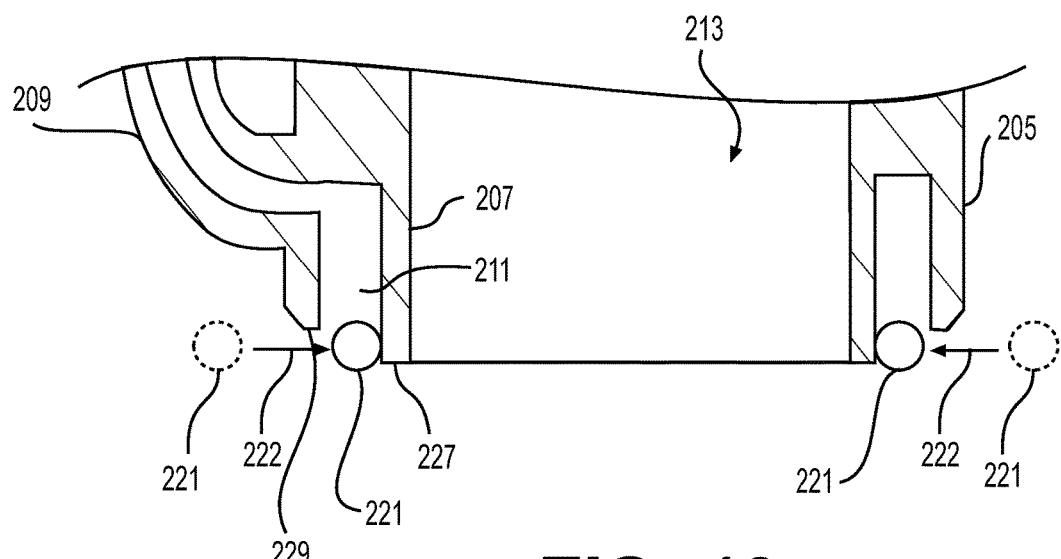
FIG. 13 shows a close-up side view of an end of the apparatus of FIG. 10, in accordance with aspects of the present disclosure.

FIG. 10 shows an exemplary tissue resection apparatus, according to an embodiment of the present disclosure. As shown, the apparatus may include a housing 203 having an outer wall 205 with a distal end 229, and an inner wall 207 with a distal end 227 (see FIG. 13). The inner wall 207 may be surrounded by the outer wall 205. The inner and outer walls 207 and 205 may be separated by a predetermined distance so that there is a hollow gap or cavity 211 formed between the inner and outer walls 207 and 205. A distal end of the cavity 211 may extend between the distal ends 227 and 229 of the inner and outer walls 207 and 205.

In one embodiment, the cavity 211 may be substantially annular. It is contemplated that the cavity 211 may be completely annular, extending completely about the housing 203. The distal end of the housing 203 may be open so that the housing 203 can be placed against a surface of tissue. In some embodiments, the space surrounded by the inner wall 207 may be hollow, forming a hollow chamber 213. The housing 203 may include a proximal opening 215, providing access to the hollow chamber 213, so that an elongated tubular member 217 can be inserted into the hollow chamber 213. Elongated tubular member 217 may include the features of elongated tubular member 17. For example, elongated tubular member 217 may include an endoscope with one or more lumens (not shown) extending therethrough for receiving one or more medical devices (not shown). Housing 203 may also include one or more ridges or ledges 219 on its radially inner surface. Ridges or ledges 219 may include the features of ridges or ledges 19, and may help position the elongated tubular member 217 within the hollow chamber 213.

The housing 203 may further include a connection to a suction source (not shown), for example a lumen 209, for applying suction in the cavity 211 to draw tissue into the cavity 211. In one embodiment, lumen 209 may be in fluid communication with cavity 211, so that negative or positive pressure applied to lumen 209 may be present throughout cavity 211. Lumen 209 may extend proximally from a distal portion of the housing 203. Lumen 209 may extend along a side surface of the housing 203, and/or along a side surface of the elongated tubular member 217.

When the apparatus is placed against the surface of targeted tissue layer "L", the negative pressure or suction applied from the suction source (not shown) via the lumen 209 may draw in the targeted tissue "L" into the cavity 211, thereby forming a ridge of tissue, as illustrated in FIG. 3. The raised ridge of tissue drawn into the cavity 211 may facilitate snaring or other resection methods. The cavity 211 may be preferably narrow so that the non-targeted sub tissue layer (e.g., tissue layer "SL") is excluded from being drawn up into the cavity, thereby reducing the risk of perforating the SL tissue layer.

The housing 203 may be annular. In some embodiments, the housing 203 may have a shape that includes at least one straight edge. For example, the housing 203 may have the shape of a housing 203' shown in FIG. 11. The housing 203' may include an inner wall 207' having a distal end 227', an outer wall 205' having a distal end 229', a cavity 211' between the inner and outer walls 207' and 205', and a lumen 209' through which a vacuum may be created in cavity 211'. Inner wall 207', outer wall 205', and/or cavity 211' may have at least one straight edge. In such an embodiment, a substantially straight portion of the tissue layer L may be drawn into the cavity 211'. It is also contemplated that inner wall 207', outer wall 205', and/or cavity 211' may be substantially rectangular. In such an embodiment, a substantially rectangular portion of the tissue layer L may be drawn into the cavity 211'. While inner and outer walls 207' and 205' are each shown with four sides, it should be understood that other numbers of sides may also be used. Further, corners of inner wall 207', outer wall 205', and/or cavity 211' may be rounded off or curved, giving housing 203' an atraumatic shape to reduce the probability of unintentionally damaging tissue with housing 203'.

Figure 12:
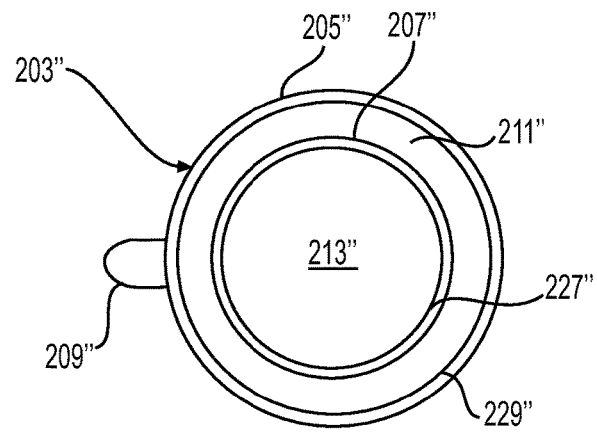
FIG. 12 shows an end view of a housing, in accordance with aspects of the present disclosure.

In other embodiments, the housing 203 may have a curved shape. For example, the housing 203 may have the shape of a housing 203" shown in FIG. 12. The housing 203" may include an inner wall 207" having a distal end 227", an outer wall 205" having a distal end 229", a cavity 211" between the inner and outer walls 207" and 205", and a lumen 209" through which a vacuum may be created in cavity 211". Inner wall 207", outer wall 205", and/or cavity 211" may have no straight sides. In such an embodiment, a curved portion of the tissue layer L may be drawn into the cavity 211". It is also contemplated that inner wall 207", outer wall 205", and/or cavity 211" may be circular or elliptical. In such an embodiment, a substantially circular or elliptical portion of the tissue layer L may be drawn into the cavity 211".

The apparatus may be equipped with a cutting tool, such as a snare 221. The snare 221 can be opened and preloaded around the outer surface of the housing 203 prior to drawing in the tissue. The tubular member 217 may be attached by an attachment member 223 to at least one auxiliary working channel 225. The auxiliary working channel 225 may include a lumen configured to receive the snare 221. When the tissue layer L is drawn into the cavity 211, the snare 221 can be closed around the base of the raised circumferential ridge of the drawn up tissue for resection. During closing of the snare 221, at least a portion of the snare 221 may enter a portion of the cavity 211 extending between distal ends 227 and 229 of the inner and outer walls 207 and 205. The direction of closing of the snare 221 is shown by arrows 222 in FIG. 13.

In some embodiments, the distal end 227 of the inner wall 207 may extend farther distally than the distal end 229 of the outer wall 205. As the snare 221 is closed around the base of the raised circumferential ridge of the drawn up tissue, the snare 221 may exert a force on the tissue and an outer surface of the inner wall 207 at the distal end 227. For example, the snare 221 may compress the tissue against the outer surface of the inner wall 207 at the distal end 227. This compression may assist with resection of the tissue. The snare 221 may be closed until it is brought into direct contact with the outer surface of the inner wall 207 at the distal end 227. The distal end 229 of the outer wall 205 may be beveled on a radially outer edge to guide the closing snare 221 into the cavity 211 and/or against the inner wall 207. It is contemplated that a ligating band or shuttling wire may be used in some embodiments, instead of snare 221.

It should be understood that this disclosure is, in many respects, only illustrative. Changes may be made in details, particularly in matters of shape, size, length, and arrangement of components without exceeding the scope of the present disclosure. Thus, the present disclosure is intended to cover alternatives, modifications, and equivalents, which may be included within the spirit and scope of the present disclosure as defined by the claims.

What is claimed is:
1. A medical device, comprising:
 a housing including:
  an outer wall having a distal end,
  an inner wall spaced from the outer wall, wherein the outer wall surrounds the inner wall; wherein the inner wall is fixedly coupled to the outer wall, wherein the inner wall has a distal end, and wherein the distal end of the outer wall is proximal to the distal end of the inner wall, and a cavity located between the outer wall and the inner wall and defined by the outer wall and the inner wall, wherein the cavity is in fluid communication with a lumen configured to adjust pressure within the cavity; and a cutting tool configured to move from extending around an outer surface of the housing to entering the cavity of the housing.

2. The medical device of claim 1, wherein the cutting tool is a snare.

3. The medical device of claim 2, wherein the snare is configured to form a loop around the outer surface of the housing.

4. The medical device of claim 3, wherein the loop is configured to enter the cavity of the housing as the loop closes.

5. The medical device of claim 1, wherein a distal end of the cavity extends from the distal end of the outer wall to the distal end of the inner wall.

6. The medical device of claim 1, wherein at least one of the distal end of the inner wall and the distal end of the outer wall includes a straight edge.

7. The medical device of claim 1, wherein at least one of the distal end of the inner wall and the distal end of the outer wall is substantially rectangular.

8. A medical device, comprising:
a housing including:
an outer wall having a distal end,
an inner wall spaced from the outer wall and fixedly coupled to the outer wall, the inner wall having a distal end, wherein the distal end of the outer wall is disposed proximally from the distal end of the inner wall, and a cavity between the outer wall and the inner wall, wherein the cavity is in fluid communication with a lumen configured to adjust pressure within the cavity; and a cutting tool configured to move from extending around an outer surface of the housing to exerting a radially inwardly directed force directly against the inner wall of the housing.

9. The medical device of claim 8, wherein the cutting tool is a snare.

10. The medical device of claim 9, wherein the snare forms a loop around the outer surface of the housing.

11. The medical device of claim 8, wherein the radially inwardly directed force is a compressive force around the inner wall of the housing.

12. The medical device of claim 8, wherein the cutting tool is configured to move into direct contact with the inner wall of the housing.

13. The medical device of claim 8, wherein at least one of the distal end of the inner wall and the distal end of the outer wall includes a straight edge.

14. The medical device of claim 8, wherein at least one of the distal end of the inner wall and the distal end of the outer wall is substantially rectangular.

* * * * *